United States Patent [19]

Ackerman

[11] Patent Number: Plant 7,437

[45] Date of Patent: Feb. 5, 1991

[54] RASPBERRY PLANT NAMED PSI 127

[75] Inventor: Stephen M. Ackerman, Salinas, Calif.

[73] Assignee: Plant Sciences, Inc., Watsonville, Calif.

[21] Appl. No.: 398,440

[22] Filed: Aug. 25, 1989

[51] Int. Cl.[5] ..... A01H 5/00

[52] U.S. Cl. ..... Plt./46

[58] Field of Search ..... Plt./46

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A distinct everbearing red raspberry variety characterized by everbearing fruit habit, high yields, producing about 40% of its overall spring floricane production in May, early fruiting habits on second year floricanes, exceptional vigor, producing twice as many suckers as Heritage, reduced thorns, and producing fruit averaging between 18.2 mm in length by 18.1 mm in width.

4 Drawing Sheets

My invention relates to a new and distinct everbearing red raspberry variety named PSI 127, botanically known as *Rubus idaeus.* It was discovered by me as a chance seedling in a breeding plot established in 1987 on a ranch in Watsonville, Calif., provided by Well-Pict, Inc., of Watsonville.

A breeding program was initiated jointly by Plant Sciences, Inc. and Coast Cooling, Inc., with the goal of developing new and distinct raspberry varieties. In 1987, my new variety, PSI 127, was selected, and extensively tested over the next year.

On Dec. 30, 1987, 15 to 20 dormant sucker canes of the variety were dug from the 1987 seedling field located on the Flats Ranch, Watsonville, Calif. All canes were hand dug as dormant root stock, cleaned, bagged and boxed. The canes were stored at a local cold storage facility at 28° F. until planting. These canes were planted on Jan. 26, 1988, in 15 to 20 linear feet of bed in the 1988 selection field, also located on the Flats Ranch.

On Nov. 30, 1988, 100 dormant sucker canes of this variety were dug from the 1988 selection field, located on the Flats Ranch, for further propagation. The following lists the planting dates, number of plants propagated and location of each planting. The variety has been reproduced through asexually propagated sucker plants from selection fields in Watsonville, Calif. These daughter plants were then re-located for further testing on local grower fields associated with Well-Pict, Inc., in the Watsonville/Salinas area. Through further tests and subsequent generations, the characteristics of the novel variety were shown to remain fixed and true to type.

| Planting Date | No. Plants | Location/Watsonville, CA |
|---|---|---|
| 12-30-88 | 40* | Peckham Ranch |
| 1-19-89 | 15** | Flats Ranch |
| 1-19-89 | 6* | Nakano Ranch |
| 1-25-89 | 20* | Peckham Ranch |
| 4-30/5-2-89 | 2,000–3,000*** | Flats Ranch |

*Planted as dormant bare root stock for field evaluations.

**Planted as dormant bare root stock for field evaluations in the 1989 advanced selection field.

***Planted for commercial nursery stock as greenhouse matured shoot tips propagated from 8–10 lbs. of roots.

The following features are particularly outstanding in my new variety:

1. Everbearing fruiting habit, fruits on first year primocanes.

2. High yields, producing about 40 percent of its overall spring production in May.

3. Early fruiting habits on second year floricanes, 2–3 weeks earlier than Willamette, and one week earlier than PSI 168 or PSI 79.

4. Exceptional vigor, producing twice as many suckers as Heritage.

5. Reduced thorns, about 50 percent smaller than Heritage.

The accompanying photographs show typical specimens of my new red raspberry variety PSI 127 at various stages of development.

Photograph 1 shows a section of a typical primocane with its many small and reduced thorns, foliage, fruit, flowers, and a typical fruiting terminal.

Photograph 2 shows the developmental stages of a berry from flower to maturity, also the purple coloration of a typical primocane.

Photograph 3 depicts a typical fruiting terminal, showing the exposure of the fruit that makes this variety very easy to pick. The FIGURE also shows the irregular shapes of the drupelets leading to irregularity of fruit shape.

Photograph 4 shows a typical mature leaf with its glossy and very reduced corrugation, and also the distinct downward cupping of the leaf.

FIG. 1 illustrates the electrophoresis pattern unique to this variety, as explained in detail below.

Production on first year primocanes begins approximately on August 1, yielding 25 percent of its total production in August, 55 percent in September, 15 percent in October, and 5 percent in November, peaking during the first week in September. Berry size averages 3.1–3.3 grams from August through November, (about 20 percent larger than Heritage).

Spring production on second year floricanes begins approximately on May 1, yielding 40 percent of its total production in May, 45 percent in June and 15 percent in July, peaking during the first of June. Berry size averages 2.3–2.5 grams from May through July, (about 20 percent smaller than Willamette).

The spring crop typically comprises 55 percent of the total production, with the fall crop comprising 45 percent. The spring crop precedes Willamette by approximately two weeks, with yields throughout the year exceeding those of both Heritage and Willamette.

The following is a detailed description of my new variety, based upon observations taken in Watsonville, Calif. Color terminology is in accordance with the Munsell Book of Colors, Munsell Color, Baltimore, Md. (1976).

Parentage: An open pollinated seedling of unknown parentage.

Fruit: Conditions when described; late (Oct. 27, 1988).

*Color.*—Red, color 7.5R 3/8 to 7.5R 3/10.

*Size.*—Averages 18.2 mm long×18.1 mm wide (2.4 grams).

*Shape.*—Ovate, tapering to a rounded tip.

*Cavity.*—Funnel shaped, size averages 14.0 mm deep×8.0 mm wide.

*Receptacle.*—Cone shaped, size averages 12.0 mm long×8.5 mm wide at the base, tapering to a sharp point. Color 10Y 9/4 to 10Y 8.5/4.

*Drupelets.*—Small, irregular in shape, averages 65–80 per berry, and 16–17 around the outer rim.

*Seeds.*—Small, average 2.5 mm long×1.3 mm wide×0.9 mm thick. Average weight, 1.3 milligrams per seed. Surface is rugose. Color tan, 10YR 8/4 to 10YR 7/4.

*Sepals.*—Acuminate, number — 5, color 5GY 6/6 to 5GY 7/6.

*Petals.*—Obovate, number — 5.

*Quality.*—Very good fresh. Holds uniformity in color and appearance through cold storage and shipping. Fruit is well exposed and easy to pick. Detaches easily from receptacle.

Plant: Data are an average of two evaluations, made on Sept. 23, 1988 and Oct. 12, 1988.

*Growth.*—Vigorous.

*Crown.*—Branched.

*Leaves.*—All samples were taken from a fully mature trifoliate, 10 to 12 trifoliates from the terminal bud. Leaves are typically smoothly rugose and glossy in appearance, with a distinct downward cupping. Foliage is nearly always trifoliate. Occasionally, the central leaflet will develop points to true independent leaflets, thus, creating a four foliate. Central leaflet: Size — averages 10.9 cm long×10.0 cm wide; Shape — cordate, tapering to an acuminate point. Color — upper surface, 7.5GY 4/4 to 7.5GY 3/4, lower surface, 5GY 7/2 to 5GY 6/2. Lateral leaflet: Size — averages 9.6 cm long×7.3 cm wide; shape-ovate, tapering to an acuminate point. Petiole: averages 4.1 to 4.3 cm long and 2.9 to 3.1 mm in diameter.

*Canes.*—Moderately tall, average from 1.5 to 1.7 meters tall, with an average basal diameter of 1.4 to 1.5 cm. Color, evaluated on Feb. 10, 1989, is light grey-brown, 7.5YR 8/2 to 7.5YR 7/2. Internode length averages 3.7 to 3.9 cm at mid cane. Produces on the upper 30 percent of its cane an average of 10 to 11 fruiting laterals, with an average length of up to 47–50 cm. Fruit is borne in raceme clusters, averaging 11 to 12 berries per terminal prior to the first trifoliate.

*Suckers.*—Produces an average of 7–9 suckers per linear foot of bed planted in a single row, spaced 12 inches apart. Average basal diameter — 0.7 to 0.8 cm. Glabrous with many small stout prickles, heavy at the base, averaging 20 per cm of cane by 2.0 mm long, to 10 per cm at the tip by 1.0 mm long. Internode length — averages 4.3 to 4.5 cm at mid cane. Color is light green, 5GY 7/4 to 5GY 6/4. With age and exposure to the sun, suckers tend toward a purple coloration, 10RP 3/8 to 10RP 6/8.

My new variety may not be resistant to any known diseases and insects. It is known to be susceptible to powdery mildew and rust. This new variety may vary slightly in description, depending upon weather, soil, location, and evaluation dates.

Studies of protein polymorphism in Rubus by the starch gel electrophoresis process have been carried out to characterize this newly developed variety and distinguish it from other varieties.

Isozymes were extracted from young leaves and characterized using starch gel electrophoresis techniques. The following isozymes were characterized: malate dehydrogenase (MDH: EC 1.1.1.37); triose phosphate isomerase (TPI: EC 5.3.1.1); phosphoglucoisomerase (PGI: EC 5.3.1.9) and phosphoglucomutase (PGM: EC 2.7.5.1).

The plant material used was both field and greenhouse grown in Watsonville, Calif. Newly matured leaves (1 g fresh weight) from the growing tips of canes were used. Samples were held at 4–8C. and analyzed within 24 hours of collection.

The tris extraction buffer (pH 8.0) was as follows: 0.05M tris base, 0.007M citric acid (monohydrate), 0.1% cysteine hydrochloride, 0.1% ascorbic acid (Na salt or free acid), 1.0% polyethylene glycol, and 80 ul/l 2-mercaptoethanol. Samples were extracted in 10–12 ml cold buffer by homogenizing at 17,000 rpm.

Gel and electrode buffers for the four enzyme systems analyzed are given in Table 1. Electrophoresis specifications for the enzyme systems are given in Table 2.

The starch gel is prepared as follows, and held overnight at 20±5C. prior to use. Potato starch (30 g) is dissolved in 80 ml of cold gel buffer (System A: gel buffer 50 ml/electrode buffer 30 ml) in a vacuum flask (1.0 l). Boiling gel buffer (220 ml) is added to the starch solution. Starch is completely dissolved by vigorously swirling the solution in the vacuum flask, and vacuumed for 15 to 30 seconds. Gel solution is immediately poured onto a 20.5×22.0 cm plexiglass gel plate and covered until use.

Samples are inoculated onto paper wicks and placed in a cooled gel (4C.); covered with Saran and electrophoresed for 20 minutes. The wicks are removed and the system is run until the dye front travels approximately 5–8 cm.

Following electrophoresis, the gel is sliced into four equal slices and stained for each enzyme system. Banding patterns are interpreted as they develop and gel slices are fixed in 50% glycerol.

TABLE 1

| SYSTEM | pH | GEL BUFFER | G/L | ELECTRODE BUFFER | G/L | pH |
|---|---|---|---|---|---|---|
| A | 8.3 | Tris Base | 65 | Lithium Hydroxide | 1.2 | 8.3 |
| | | Citric Acid (Monoh) | 1.5 | Boric Acid | 12.0 | |
| B | 7.0 | DL-Histidine HCL (Monohydrate) | 1.2 | Tris Base | 16.5 | 7.0 |
| | | | | Citric Acid (Monohyd.) | 9.0 | |
| C | 7.8 | Tris Ultra Pure | 1.09 | Tris Ultra Pure | 16.35 | 7.8 |
| | | Citric Acid | 0.63 | Citric Acid | 9.03 | |

TABLE 1-continued

| SYSTEM | pH | GEL BUFFER | G/L | ELECTRODE BUFFER | G/L | pH |
|---|---|---|---|---|---|---|
| | | $Na_2EDTA$ | 0.45 | $Na_2EDTA$ | 0.45 | |

TABLE 2

RUBUS ELECTROPHORESIS SPECIFICATIONS

| SYSTEM | ENZYME | pH | CURRENT | GEL SLICE # |
|---|---|---|---|---|
| A | PGI | 8.3 | 275V | 2 |
| A | LAP | 8.3 | 275V | 4 |
| B | MDH | 7.0 | 150V | 2 |

TABLE 2-continued

RUBUS ELECTROPHORESIS SPECIFICATIONS

| SYSTEM | ENZYME | pH | CURRENT | GEL SLICE # |
|---|---|---|---|---|
| B | PGM | 7.0 | 150V | 3 |
| C | TPI | 7.8 | 50 mA | 2 |

The isozyme banding patterns for the variety PSI 127, as compared to those of Heritage, are given in FIG. 1. The RF value is the ratio of the distance (cm) traveled by the band to the distance traveled by the dye front (cm).

What is claimed is:

1. A new distinct variety of red raspberry plant named PSI 127, as herein described and illustrated.

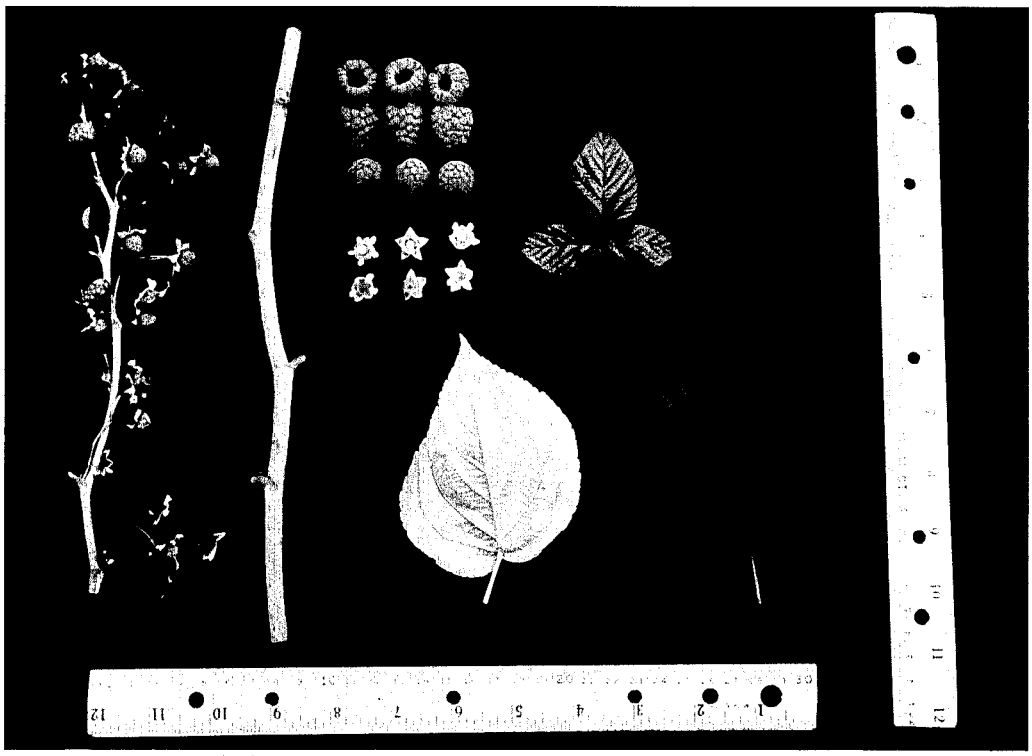

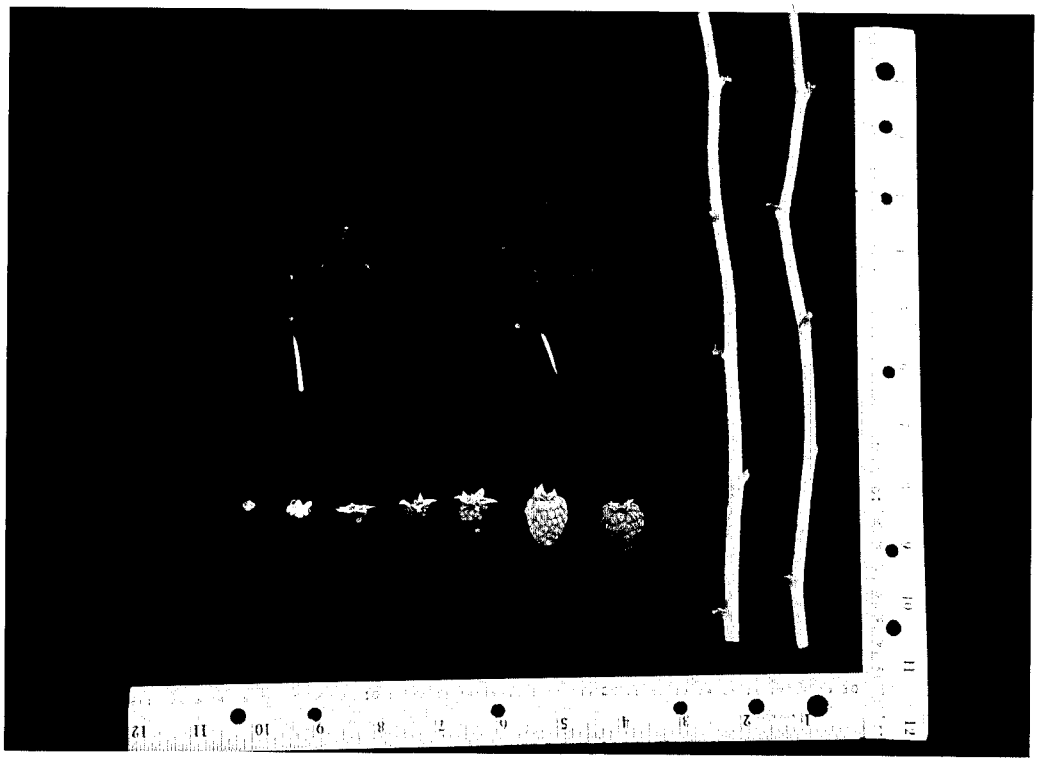

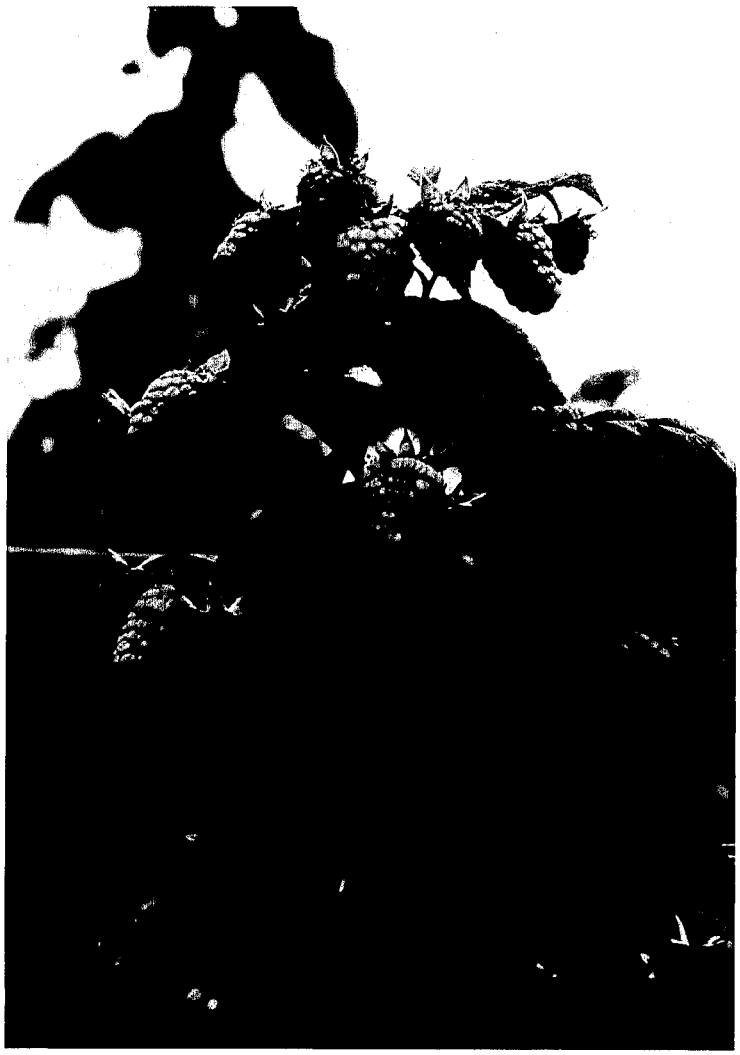

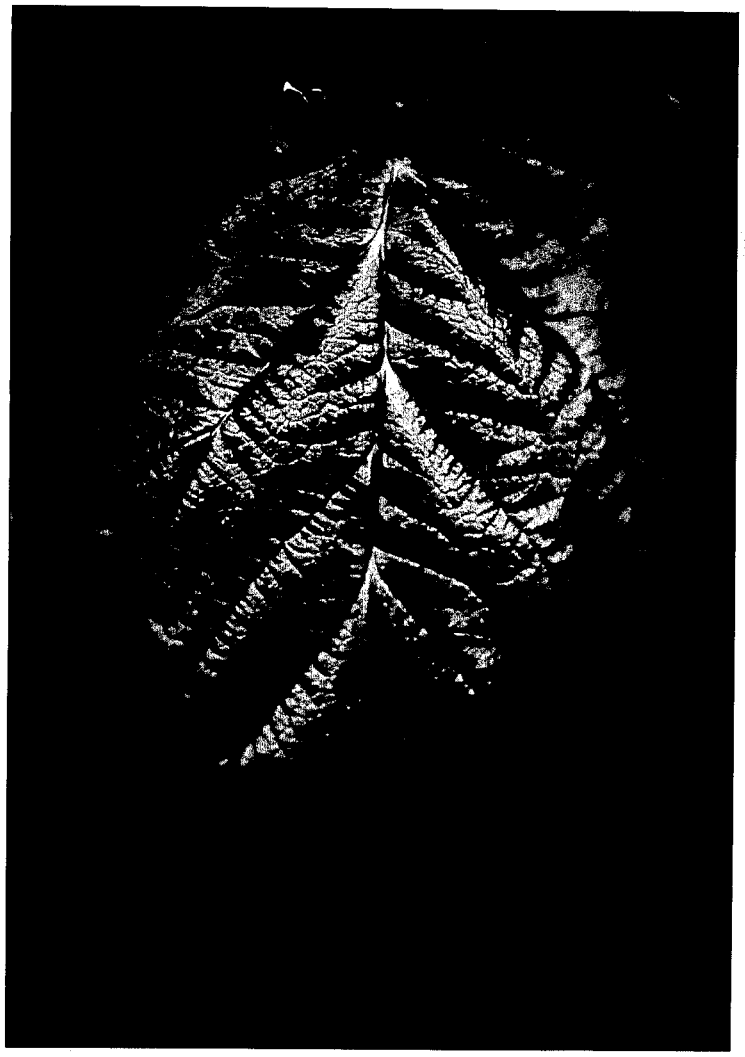

* * * * *